US008404751B2

(12) United States Patent  
Birnbaum et al.

(10) Patent No.: US 8,404,751 B2  
(45) Date of Patent: Mar. 26, 2013

(54) SUBUNGUICIDE, AND METHOD FOR TREATING ONYCHOMYCOSIS

(75) Inventors: Jay E. Birnbaum, Montville, NJ (US); Keith A. Johnson, Durham, NC (US)

(73) Assignee: Hallux, Inc., Santa Ana, CA (US)

( * ) Notice: Subject to any disclaimer, the term of this patent is extended or adjusted under 35 U.S.C. 154(b) by 233 days.

(21) Appl. No.: 12/606,324

(22) Filed: Oct. 27, 2009

(65) Prior Publication Data

US 2010/0048724 A1    Feb. 25, 2010

Related U.S. Application Data

(63) Continuation-in-part of application No. 11/523,508, filed on Sep. 19, 2006, now abandoned, which is a continuation-in-part of application No. 10/671,307, filed on Sep. 25, 2003, now Pat. No. 7,135,194.

(60) Provisional application No. 60/414,012, filed on Sep. 27, 2002.

(51) Int. Cl.
*A01N 33/02* (2006.01)
*A61K 9/14* (2006.01)
*A61K 8/18* (2006.01)
*A61K 31/497* (2006.01)
*A61N 1/30* (2006.01)

(52) U.S. Cl. ..... 514/655; 424/484; 424/61; 514/253.07; 604/20

(58) Field of Classification Search ............ None
See application file for complete search history.

(56) References Cited

U.S. PATENT DOCUMENTS

| 4,144,346 A | 3/1979 | Heeres et al. |
| 4,180,058 A | 12/1979 | Brem |
| 4,223,036 A | 9/1980 | Heeres et al. |
| 4,250,164 A | 2/1981 | Bernstein |
| 4,263,289 A * | 4/1981 | Edwards ............ 514/179 |
| 4,267,179 A | 5/1981 | Heeres et al. |
| 4,404,216 A | 9/1983 | Richardson |
| 4,490,395 A * | 12/1984 | Cherukuri et al. ......... 426/3 |
| 4,636,520 A | 1/1987 | Umio et al. |
| 4,957,730 A | 9/1990 | Bohn et al. |
| 5,002,938 A | 3/1991 | Wang et al. |
| 5,063,049 A | 11/1991 | Billings |
| 5,110,809 A | 5/1992 | Wang et al. |
| 5,120,530 A | 6/1992 | Ferro et al. |
| 5,219,877 A | 6/1993 | Shah et al. |
| 5,264,206 A | 11/1993 | Bohn et al. |
| 5,346,692 A | 9/1994 | Wohlrab et al. |
| 5,391,367 A | 2/1995 | DeVincentis et al. |
| 5,422,370 A | 6/1995 | Yu et al. |
| 5,464,610 A | 11/1995 | Hayes, Jr. et al. |
| 5,487,776 A | 1/1996 | Nimni |
| 5,547,988 A | 8/1996 | Yu et al. |
| 5,597,849 A * | 1/1997 | McGinity et al. ............ 514/648 |
| 5,696,105 A * | 12/1997 | Hackler ............ 514/172 |
| 5,894,020 A | 4/1999 | Concha |
| 6,008,173 A * | 12/1999 | Chopra et al. ............ 510/152 |
| 6,043,063 A | 3/2000 | Kurdikar et al. |
| 6,143,794 A | 11/2000 | Chaudhuri et al. |
| 6,162,420 A | 12/2000 | Bohn et al. |
| 6,207,142 B1 | 3/2001 | Odds et al. |
| 6,221,903 B1 | 4/2001 | Courchesne |
| 6,224,887 B1 | 5/2001 | Samour et al. |
| 6,231,840 B1 | 5/2001 | Buck |
| 6,264,927 B1 | 7/2001 | Monahan |
| 6,361,785 B1 | 3/2002 | Nair et al. |
| 6,733,751 B2 | 5/2004 | Farmer |
| 6,846,837 B2 | 1/2005 | Maibach et al. |
| 6,878,365 B2 * | 4/2005 | Brehove ............ 424/61 |
| 7,074,392 B1 | 7/2006 | Friedman et al. |
| 2002/0173436 A1 | 11/2002 | Sonnenberg et al. |
| 2002/0183387 A1 | 12/2002 | Bogart |
| 2003/0007939 A1 | 1/2003 | Murad |
| 2003/0207971 A1 * | 11/2003 | Stuart et al. ............ 524/274 |
| 2004/0062733 A1 | 4/2004 | Birnbaum |
| 2006/0112503 A1 | 6/2006 | Hatano et al. |

FOREIGN PATENT DOCUMENTS

EP    0024587 A1    3/1981
WO    98/52927 A1    11/1998

OTHER PUBLICATIONS

Nesci, A., et al., "Control of Aspergillus growth and aflatoxin production using antioxidants at different conditions of water activity and pH", 2003, J. Applied Microbio., 95, pp. 279-287.*
American Academy of Dermatology, "International Study Measures Quality of Life for Onychomycosis Patients," Sep. 22, 1999.
Stedman's Medical Dictionary 27th Edition, "hyponychium", downloaded from http://www.thomsonhc.com/pdrel/librarian/PFDefaultActionId/pdrcommon.Stedmans, on May 4, 2006.
USP DI, "Drug Information for the Health Care Professional," 1997, 17th edition, pp. 80-83, vol. 1, the United States Pharmacopeial Convention, Inc., Rockville, MD.
Physicians GenRx—The Complete Drug Reference, 1996, pp. 88-91, Mosby-Year Book, Inc., St. Louis, MO.
Jackson A. Como and William E. Dismukes, "Oral Azole Drugs As Systemic Antifungal Therapy," The New England Journal of Medicine, Jan. 27, 1994, pp. 263-272, vol. 330, issue No. 4, Massachusetts Medical Society, Boston, MA.

* cited by examiner

*Primary Examiner* — Michael G Hartley
*Assistant Examiner* — Lance Rider
(74) *Attorney, Agent, or Firm* — Baker & Hostetler LLP

(57) ABSTRACT

Onychomycosis is a fungal infection of the nail bed and is difficult to treat topically because penetration of the nail plate is difficult, and systemic antifungal treatments are prone to side effects and drug interactions. The present invention treats onychomycosis by applying an antifungal composition to the nail bed directly using a solid, semi-solid, or flowable carrier. The carrier can be in the form of a semi-solid into which the user digs and scrapes the nail, a solid carrier can be inserted directly under the nail in contact with the nail bed, or a flowable composition can be injected in contact with the nail bed.

3 Claims, 6 Drawing Sheets

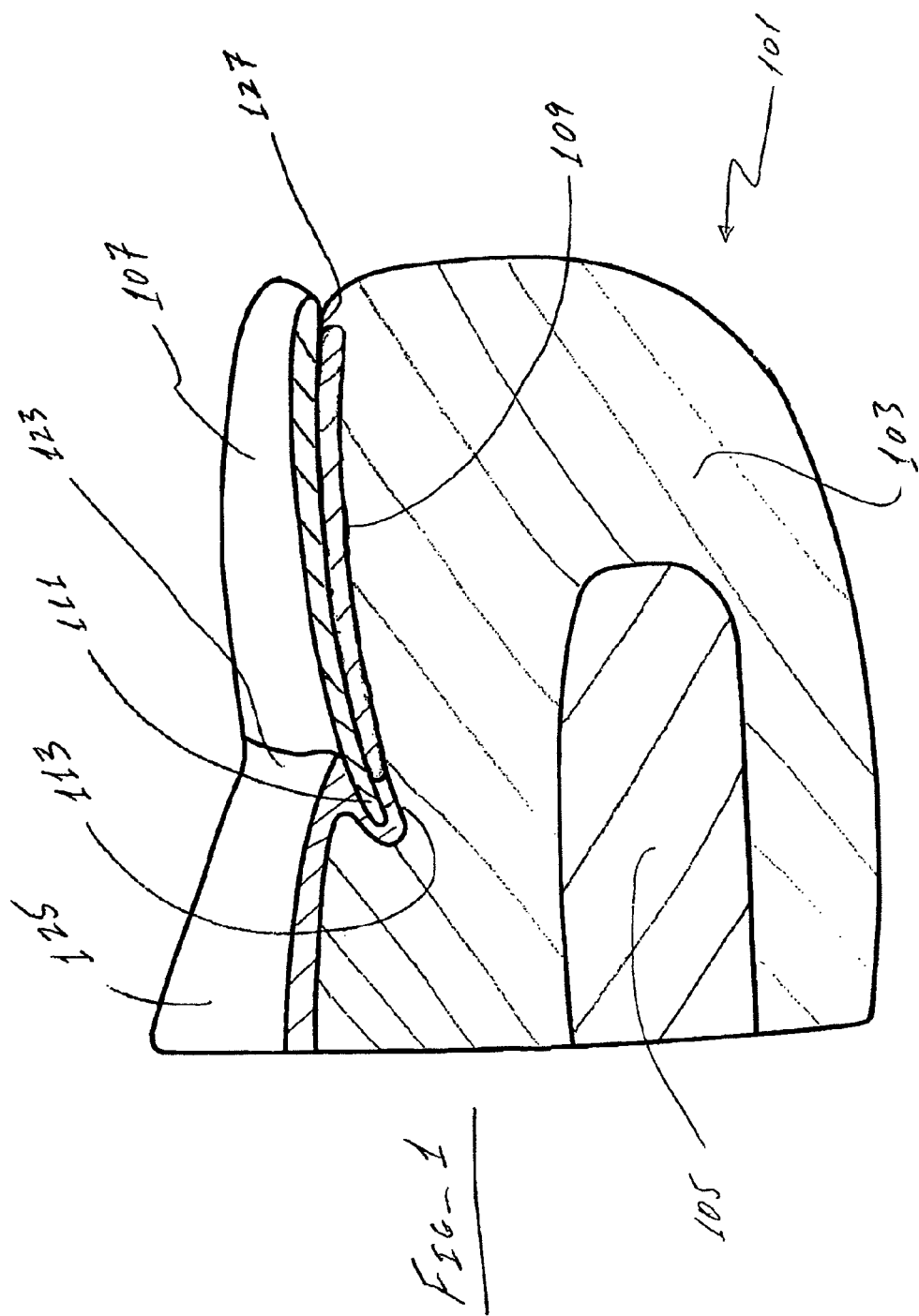

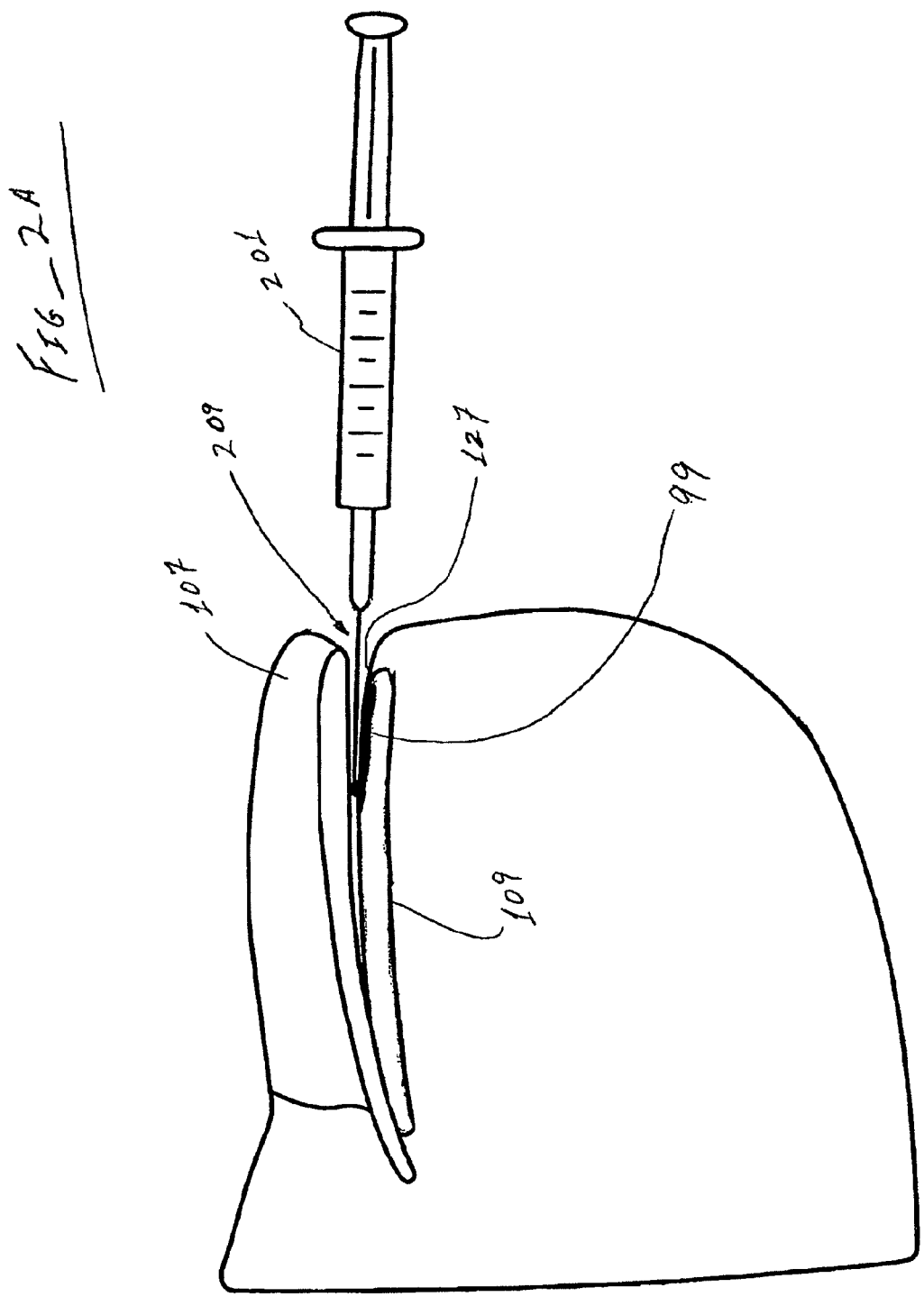

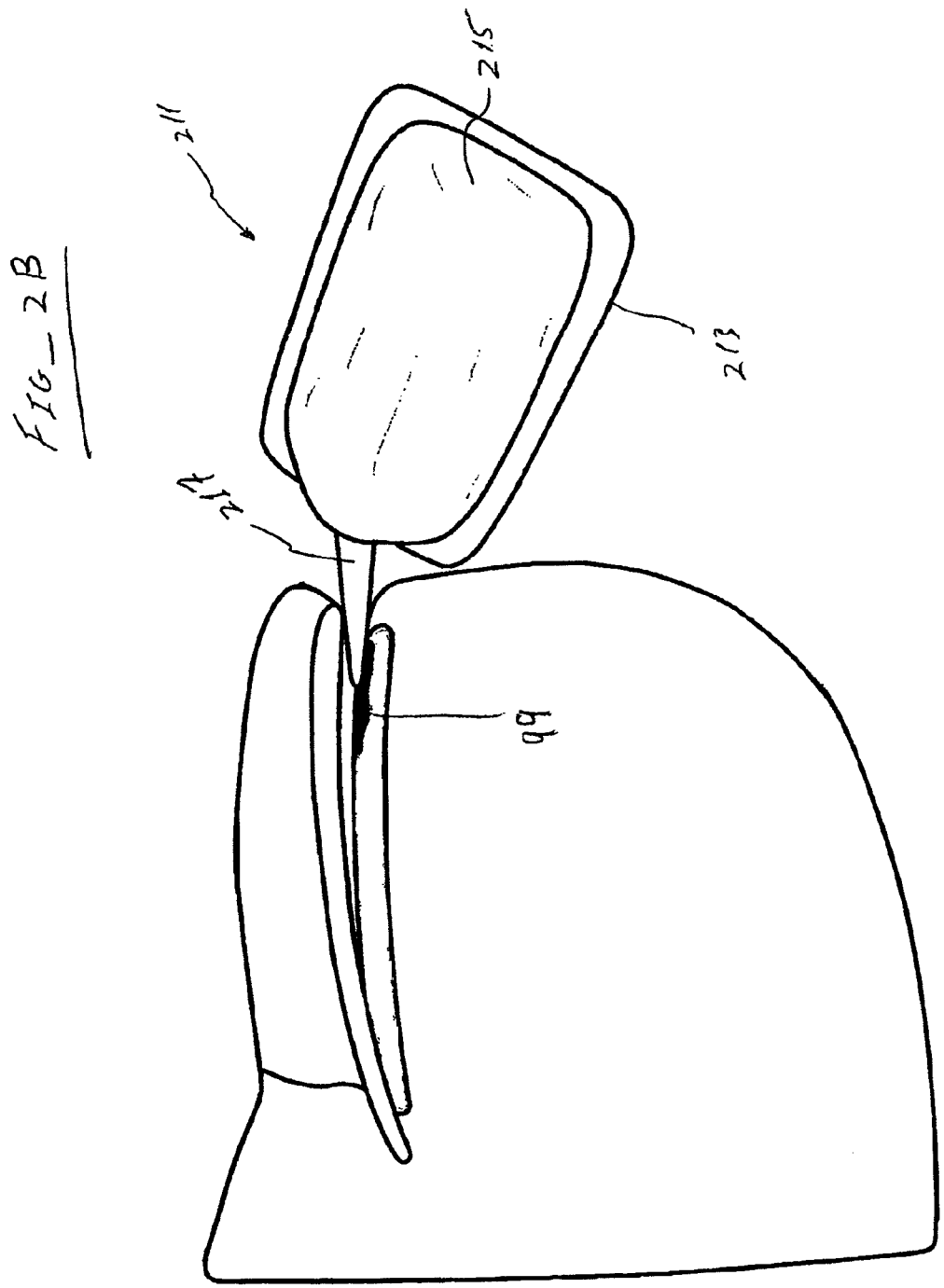

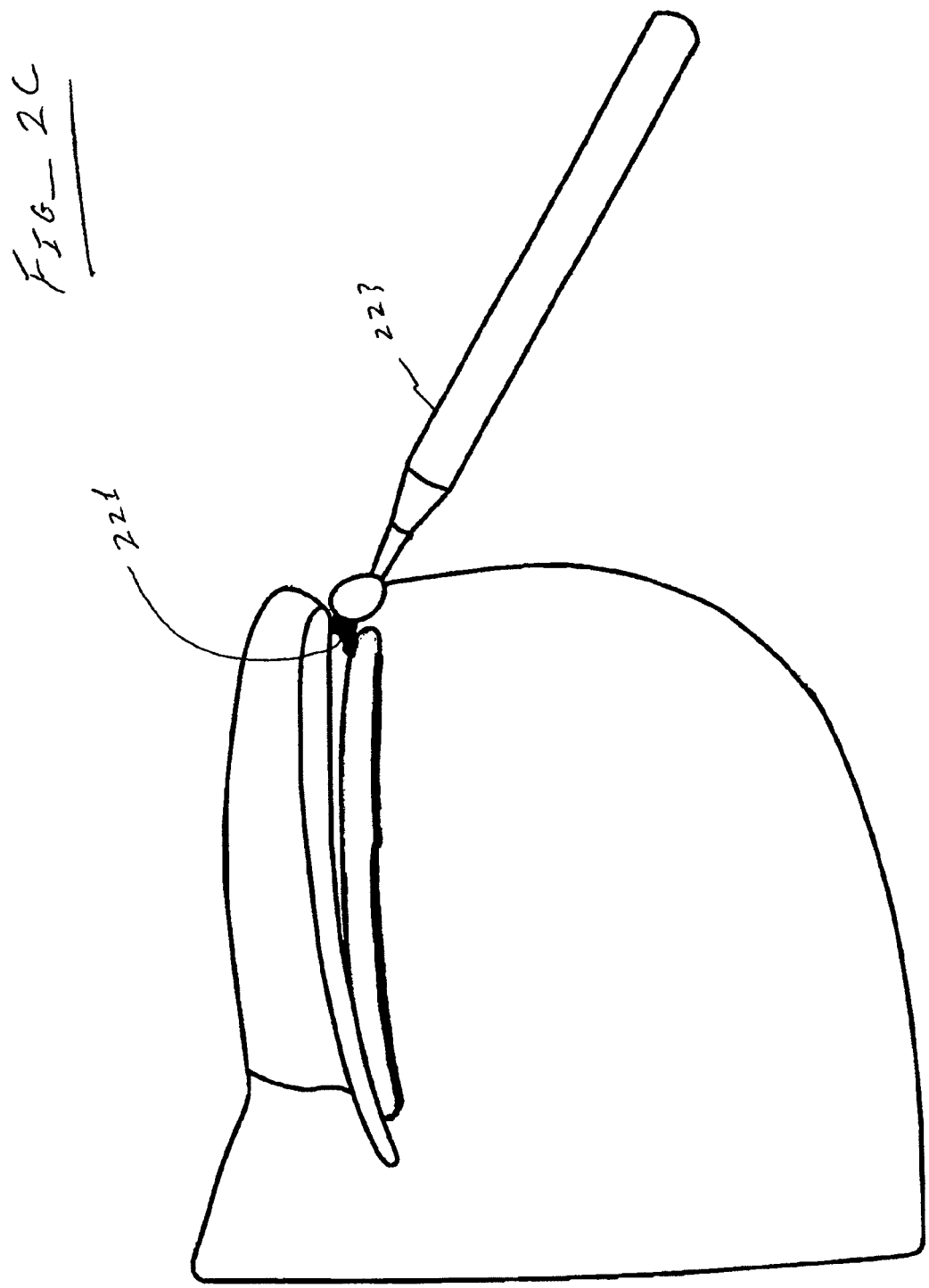

SUBUNGUICIDE, AND METHOD FOR TREATING ONYCHOMYCOSIS

RELATED INVENTIONS

This application claims priority to and is a continuation-in-part of U.S. application Ser. No. 11/523,508, filed 19 Sep. 2006, now abandoned entitled, "Subunguicide, and Method for Treating Onychomycosis," which claims priority to and is a continuation-in-part of U.S. application Ser. No. 10/671,307, filed 25 Sep. 2003, entitled, "Subunguicide, and Method for Treating Onychomycosis," now U.S. Pat. No. 7,135,194, which claims priority to U.S. Provisional Application No. 60/414,012, filed 27 Sep. 2002, entitled, "Subunguicide, and Method for Treating Onychomycosis", the disclosures of which are incorporated herein by reference.

BACKGROUND OF THE INVENTION

1. Field of the Invention

This invention relates to articles of manufacture and to methods for the subungual (under the nail) treatment of infections, especially fungal infections, of the toenails and fingernails (onychomycosis).

2. The State of the Art.

Fungi are eukaryotic cells that may reproduce sexually or asexually and may be biphasic, with one form in nature and a different form in the infected host. Fungal diseases are referred to as mycoses.

A fungal infection of the nails, commonly referred to as onychomycosis, is most frequently caused by dermatophytes but also can be caused by molds and *Candida*. Mixed infections also occur. Onychomycosis includes dermatophyte infection of the nail by any fungus, including yeast or molds. Thus, for example, onychomycosis serves as a reservoir for dermatophytes and contributes to treatment failure and recurrence of tinea pedis. Most common causes of tinea unguium are *Trichophyton rubrum* (most frequently), *T. mentagrophytes*, and *Epidermophyton floccusum*. These are dermatophytes (fungi that infect hair, skin, and nails) and feed on keratinized (nail) tissue. The nail infections they cause are normally confined to the nail bed and nail plate, but occasionally spread to the surrounding skin. Another type of onychomycosis is caused by yeast (e.g., *Candida albicans* or *Candida parapsilosis*). These infections are less common and produce similar symptoms.

The majority of known antifungal agents fall into one of three main groups. One major group includes polyene derivatives, including amphotericin B and the structurally related compounds nystatin and pimaricin, which are only administered intravenously. These are broad-spectrum antifungals that bind to ergosterol, a component of fungal cell membranes, and thereby disrupt the membranes, leading to cell death. Amphotericin B is usually effective for systemic mycoses, but its administration is limited by toxic effects that include fever and kidney damage, and other accompanying side effects, such as anemia, low blood pressure, headache, nausea, vomiting and phlebitis. The unrelated antifungal agent flucytosine (5-fluorocytosine, a diazine), an orally absorbed drug, is frequently used as an adjunct to amphotericin B treatment for some forms of candidiasis and cryptococcal meningitis. Its adverse effects include bone marrow depression with leukopenia and thrombocytopenia.

A second major group of antifungal agents includes azole derivatives which impair synthesis of ergosterol and lead to accumulation of metabolites that disrupt the function of fungal membrane-bound enzyme systems (e.g., CYP-26, i.e., cytochrome P450) and inhibit fungal growth. Significant inhibition of mammalian CYP-26 results in important drug interactions. This group of agents includes ketoconazole (U.S. Pat. Nos. 4,144,346 and 4,223,036), fluconazole (U.S. Pat. No. 4,404,216), itraconazole (U.S. Pat. No. 4,267,179), liarozole, irtemazol, clotrimazole, miconazole, econazole, butoconazole, oxiconazole, sulconazole, and terconazole. U.S. Pat. No. 6,277,873 describes substituted thiazole, thiadiazole, and oxadiazole antifungals.

Antifungal azoles are fungistatic, not fungicidal, which has resulted in azole resistant fungi, that is, fungi strains and isolates which are resistant to treatment with Fluconazole and other known antifungal agents (*New Engl. J. Med.*, 1944, 330:263-272). The small concentration of topical antifungal agents penetrating the nail through to the bed might contribute to the development of fungi resistant to therapeutic agents.

A third major group of antifungal agents includes the fungicidal allylamines such as naftifine (Naftin™), terbinafine (EP 24,587-A1; Lamisil™), and the benzylamine butenafine (Mentax™).

Yet another antifungal is the commonly used thiocarbonate tolnaftate. Like the allylamines and azoles, tolnaftate blocks synthesis of ergosterol.

Various other types of antifungal agents are known. Griseofluvin is a fungistatic agent which is administered orally for fungal infections of skin, hair or nails that do not respond to topical treatment. U.S. Pat. No. 6,221,903 describes the use of Amiodarone, a Class III antiarrhythmic drug (Amiodarone in Physicians GenRx, 1996, BeDell, et. al., eds., Mosby-Year Book, Inc., St. Louis, Mo.; Amiodarone in Drug Information for the HealthCare Profession, 1997, USP DI, Twinbrook Parkway, Md.; pp. 80-83), as an antifungal agent. Still other antifungal agents include ciclopirox, sulbentine, and morpholines, e.g., amorolfine, and the related morpholines disclosed in U.S. Pat. No. 5,120,530, and the 1-hydroxy-2-pyridone compounds disclosed in U.S. Pat. No. 4,957,730.

It has also been known to combine antifungal agents with anti-inflammatory agents. The steroidal anti-inflammatory agent may be selected from among any of the known steroidal anti-inflammatory agents, including, for example, any of those disclosed in *The Merck Index* or in U.S. Pat. Nos. 5,002,938, 5,110,809, and 5,219,877. Examples of steroidal anti-inflammatory agents useful in combination with antifungals can include 21-acetoxypregnenolone, alclometasone or its dipropionate salt, algestone, amcinonide, beclomethasone or its dipropionate salt, betamethasone and salts thereof, including, for example, betamethasone benzoate, betamethasone dipropionate, betamethasone sodium phosphate, betamethasone sodium phosphate and acetate, and betamethasone valerate; clobetasol or its propionate salt, clocortolone pivalate, hydrocortisone and salts thereof, including, for example, hydrocortisone acetate, hydrocortisone butyrate, hydrocortisone cypionate, hydrocortisone phosphate, hydrocortisone sodium phosphate, hydrocortisone sodium succinate, hydrocortisone tebutate and hydrocortisone valerate; cortisone acetate, desonide, desoximetasone, dexamethasone and salts thereof, for example, acetate and sodium phosphate; diflorasone diacetate, fludrocortisone acetate, flunisolide, fluocinolone acetonide, fluocinonide, fluorometholone, flurandrenolide, halcinonide, medrysone, methylprednisolone and salts thereof, e.g., acetate, sodium succinate; mometasone furoate, paramethasone acetate, prednisolone and salts thereof, e.g., acetate, diethylaminoacetate, sodium phosphate, sodium succinate, tebutate, trimethylacetate; prednisone, triamcinolone and derivatives thereof, e.g., acetonide, benetonide, diacetate, hexacetonide.

Other glucocorticoid steroids reported in the literature, including *The Merck Index*, or otherwise approved by the local drug regulatory agency, e.g., Food and Drug Administration, may also be used. Preferred steroidal anti-inflammatory agents usually include clobetasol and its salts, e.g., propionate salt; betamethasone and its salts, hydrocortisone and its salts, and triamcinolone and its salts, although as new steroidal anti-inflammatories are developed and reviewed, preferences may change. The anti-inflammatory agent will usually be present in a topical composition in combination with an antifungal in an amount within the range of 0.01 to about 5 percent, preferably from about 0.1 to 2 percent, based on the total weight of the composition.

Thus, various types of antifungal agents and their combination with steroidal anti-inflammatory agents are known.

In spite of the wide varieties of anti-fungal and fungistatic agents, and their use in combination with other active ingredients, onychomycosis is difficult to treat. Since most onychomycosis (i.e., the distal subungual form) is a disease of the nail bed underlying the nail plate, the condition is best treated systemically (from the inside) because topical access to the nail bed is not present. Accordingly, most onychomycosis is treated using oral medications such as terbinafine (Lamisil™) and itraconazole (Sporonox™). The nail grows slowly, and so systemic (oral) medicines require several months for elimination of the infection and regrowth of new nail. These drugs may also produce serious side effects, and they may interact with other medications. Accordingly, systemic medications for treating onychomycosis are unacceptable for many patients. For those patients, the only available route of administration is topical.

Nail lacquers for the treatment of onychomycoses and similar fungal infections affecting nails (toe nails and/or finger nails) of humans, in particular, or other animals, are known. Representative examples are described in the patent literature, such as the following U.S. Pat. No. 4,957,730 (1-hydroxy-2-pyridone in water-insoluble film-former); U.S. Pat. No. 5,120,530 (amorolfine in quaternary ammonium acrylic copolymer); U.S. Pat. No. 5,264,206 (tioconazole, econazole, oxiconazole, miconazole, tolnaftate, naftifine hydrochloride, in water-insoluble film-former); U.S. Pat. No. 5,346,692 (with urea and dibutyl phthalate plasticizer); U.S. Pat. No. 5,487,776 (griseofulvin as colloidal suspension). U.S. Pat. No. 6,224,887, teaches a nail lacquer for onychomycosis with a combination of antifungal and a certain penetration-enhancing medium carbon chain dioxane or acetal. PENLAC™ brand Ciclopirox™ is the only FDA-approved topical treatment approved in the United States for onychomycosis.

Other U.S. patent Nos. which relate to antifungal products include, for example: U.S. Pat. No. 4,636,520 (combination of imidazole and pyrrolnitrin); U.S. Pat. No. 5,002,938 (gel, combination of imidazole and 17-ester corticosteroid anti-inflammatory agent); 5,110,809 (antifungal gel plus steroid); 5,219,877 (gel product with imidazole antifungal optionally with steroidal anti-inflammatory, in a vehicle system that includes lauryl alcohol); U.S. Pat. No. 5,391,367 (aqueous alcoholic gel with tioconazole); U.S. Pat. No. 5,464,610 (salicylic acid plaster); and U.S. Pat. No. 5,696,105 (mometasone furoate).

U.S. Pat. No. 6,207,142 describes antifungal shampoos.

U.S. Pat. No. 5,894,020, discloses an antifungal bar soap for treating tinea pedis.

Anatomically, the "nail" that is seen is technically the nail plate. As shown in FIG. 1, a perspective cross-sectional view of the proximal part of a digit 101, soft tissue 103 overlies the distal phalanx 105 (not shown in other figures), and the majority and distal end of the nail plate 107 overlies the most proximal part of the nail bed 109; the root 111 of the nail plate overlies the nail matrix 113 from which the nail grows. The eponychium 123 (the cuticle) forms a seal between the skin 125 and the proximal end of the nail plate. At the distal end, between the nail plate and the skin, is the hyponychium 127, which is a physical barrier sealing the distal margin of the nail bed where it is coextensive with the nail plate. The nail plate presents a considerable barrier to dorsal (orthogonal) penetration and hence limits access to the nail bed for drugs intended for the nail bed and applied topically to the nail plate. Current topical therapies have such low penetration through the nail plate that they have a very low efficacy (less than 10% even after prolonged application). These therapies do not appear to exhibit characteristic concentration-response or time-response relationships. This suggests that in the small percentage of people in whom these topical treatments are effective, efficacy may not be related to penetration through the nail. Materials such as urea increase the penetration of the medication through the nail plate, but such materials alter the nail and disrupt its integrity.

SUMMARY AND OBJECTS OF THE INVENTION

In light of the forgoing, it would benefit the treatment of onychomycosis to administer an antifungal agent in closer proximity to the nail bed, and to decrease the barriers to access to the nail bed to treat the condition. As mentioned above, there is only a small population that is helped by topical treatment in spite of low penetration through the nail plate. This invention provides a more direct approach to topical treatment, especially in cases where not more than the distal half of the nail bed is involved, by providing a subungual treatment.

In accordance with one embodiment of the present invention, a non-liquid subunguicide is provided, which can comprise an antifungal agent and a non-soap semisolid carrier comprising a combination of a wax and an oil.

In accordance with another embodiment of the present invention, a liquid subunguicide is provided, which can comprise an antifungal agent and a liquid carrier consisting essentially of a combination of silicone oils and an alcohol solvent having not more than four carbon atoms.

In accordance with yet another embodiment of the present invention, a liquid subunguicide is provided, which can comprise an antifungal agent and a liquid carrier consisting essentially of a diester of a short chain diacid and a short chain alcohol, and optionally a non-volatile polar solvent.

In accordance with still another embodiment of the present invention, is a method for treating onychomycosis in an affected digit, which can include providing a subunguicide including an antifungal agent in a suitable solid or semi-solid carrier, and administering the same subungually by forcing the subunguicide between the hyponychium and the nail plate and past the hyponychium to be in contact with the nail bed, and heating the distal region of the digit containing the applied subunguicide to between about 32° C. and about 37° C.

BRIEF DESCRIPTION OF THE DRAWINGS

FIG. 1 is an idealized section through the distal portion of a digit depicting the anatomy.

FIGS. 2A through 2D depict the administration of a subunguicide by different devices.

DESCRIPTION OF SPECIFIC EMBODIMENTS

Figure 2D:
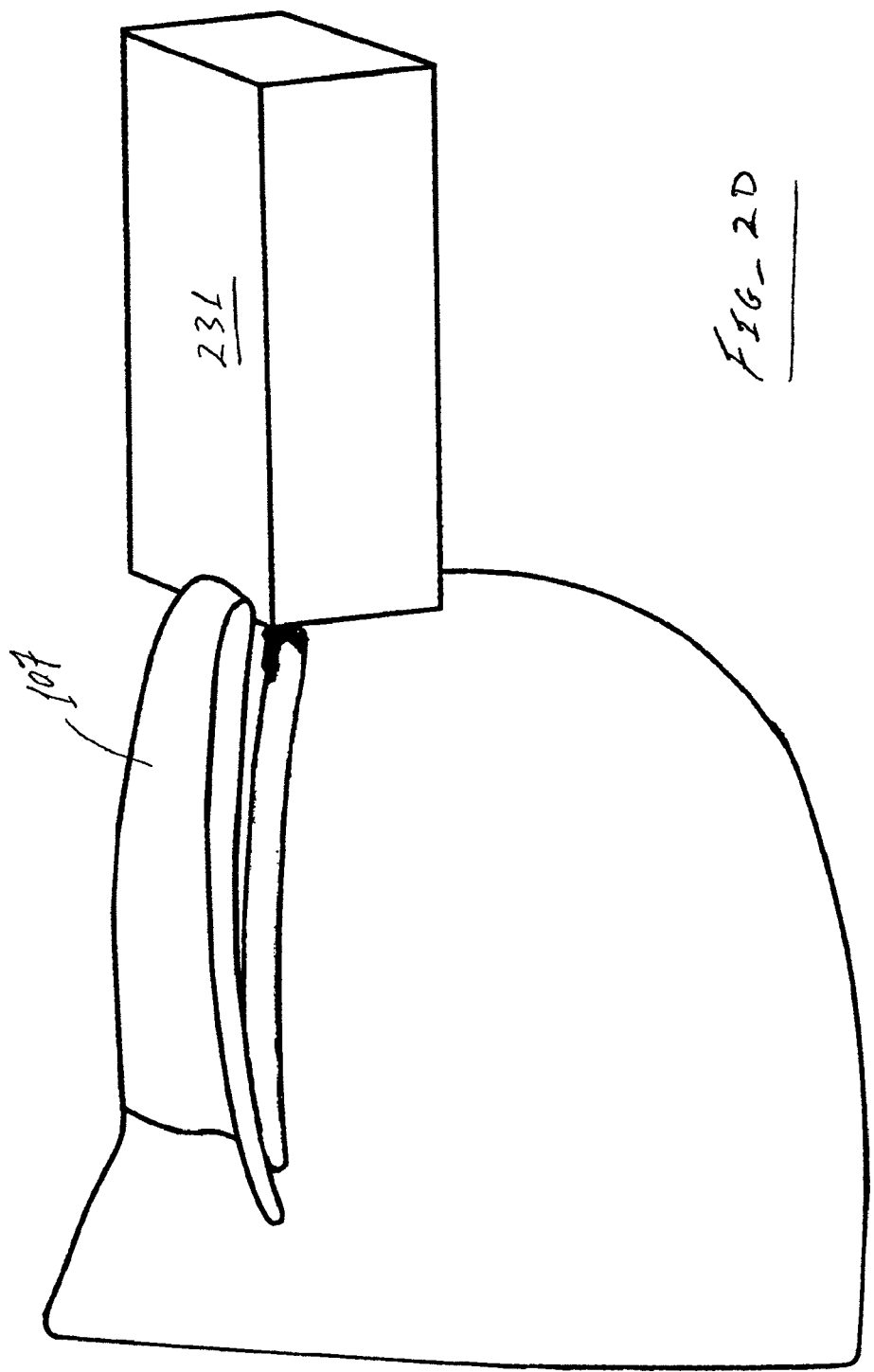

By this invention, a solid or semisolid material having a fungicidal or fungistatic agent (i.e., an antifungal or antifungal agent) is placed in contact with the nail bed and preferably forced under the nail plate to contact the nail bed. Placing the antifungal in such close proximity to the nail bed provides the preferred direct contact between the infected area and the therapeutic antifungal agent. In addition, having a small reservoir of antifungal agent in contact with the nail bed under the nail plate facilitates diffusion of antifungal proximally and/or laterally along the nail bed. Localized therapy in this fashion avoids problems with the present therapies based on systemic administration because systemic administration can increase the possibility of side effects from the systemic antifungal being manifest, as well as potential interactions with concomitant medications administered systemically and/or topically.

As one example, bar soap is commercially available having a desired antifungal agent (such as zinc pyrithione), or combination of antifungal agents, and, according to this invention, optional other active agents (e.g., an anti-inflammatory, a keratolytic agent, an anesthetic, and/or a preservative (e.g., benzyl alcohol, which also has anesthetic properties) and/or inactive agents (e.g., a colorant, fragrance, conditioner, and/or humectant). Such a product is used according to this invention by having the patient scratch the bar with the infected nail(s) effective to cause the soap shavings to reside under the nail and in contact with the nail bed. The antifungal agent can be suspended in any sort of soft solid or semisolid material, and/or it can be dispersed as solid particles. The physical properties of the solid or semisolid multidose bar, such as hardness (within the range of hardnesses that soaps can be manufactured; hardness being measured on a scale such as the Mohs hardness scale, and softer than a human nail) can be adjusted to facilitate the penetration of the soap under the nail. The bar matrix carrier for the antifungal can be a material that softens or even one that melts slowly at the surface temperature under the nail. Semisolid carriers (such as used for deodorants and antiperspirants, and cosmetics) can be formulated as desired to deliver the antifungal by having the patient scratch the substance (whether or not in the geometry of a bar).

Topical excipients can be selected from among hydrogenated castor oil, stearyl alcohol, sodium stearate, stearic acid and alcohol, cetyl wax esters, microcrystalline wax, hydrogenated vegetable oil (HVO), and PEG 3350. Considerations for selection include consistency after melting and the ability to mold into particular geometries that can later be demolded handled during commercial production.

A caulk or paste, or a gel, can be forced under the nail. The rheology of such a material can be adjusted to facilitate its being forced subungually between the nail plate and the nail bed when dispensed as it experiences different shear rates when under the nail confines than when flowing through a dispenser outlet or forced in with a spatula.

A more flowable composition, such as a cream, ointment, solution, or suspension can be placed under the nail by means of an applicator inserted between the nail bed and the nail plate. Such an applicator can be a hypodermic needle or similar device for injecting by pressure, a cannula through which a sponge or other porous carrier is inserted, or other small tube through which the antifungal may be carried.

In an analogous manner, a small strip or pellet can be placed under the nail in contact with the nail bed, or forced between the nail plate and the nail bed. The strip or pellet can be a polymer coated with an antifungal, or a hard sponge or porous polymer coated and/or infiltrated with an antifungal, or any other excipient sufficiently hard to be placed under the nail, and preferably to be forced at least partially between the nail plate and the nail bed.

For those administration devices that can be forced between the nail plate and the nail bed, the addition of a topical anesthetic and/or short-acting vasoconstrictor (to minimize bleeding) may be desirable.

Thus, while the prior art attempts to treat the condition systemically, through the nail plate, or "transungually," the present invention accesses the nail bed by administration between the hyponychium and the nail plate to so that the drug rests in contact with the nail bed. During onychomycosis, onycholysis, or lifting of the nail plate from the nail bed, is a frequent occurrence. Onycholysis occurs because of a rapid cell turnover of the nail bed epithelium, caused by the inflammatory response to the onychomycotic fungal infection. This onycholysis can be beneficial to the subungual delivery methods and compositions disclosed herein by providing some space between the nail plate and the hyponychium, allowing the medication to be forced past (over) the hyponychium and administered to the distal part of the nail bed less invasively, from where it will diffuse or migrate proximally and laterally.

Yet another method for delivering the medication is with a jet injector (high pressure injection). Such devices are typically used for insulin (by diabetes mellitus patients) and for innoculations, and force the liquid substance to be delivered through the skin. For the present invention, a jet injector, preferably having a nozzle suitable for contact with the hyponychium, can be used to administer the medication directly to the nail bed.

After administration of the medication, the subungual area can be occluded, such as with a small bandage (physical and/or a film-forming substance). A finger cot or a glove (for a hand or foot (e.g., a sock with separate extensions for each toe)) can be used to occlude the end of the digit, or multiple digits.

The amount of the active antifungal agent or mixture of such agents in the composition will depend on such factors as its structure and antimicrobial activity, release rate from the gel/paste/semisolid/solid carrier, and its diffusion characteristics. Generally, the effective amount of the antifungal agent in any given dose will be several to several tens to hundreds of times greater than the Minimal Inhibitory Concentration (MIC). Typically, amounts of active antifungal agent in the range of from about 0.5 to 20 percent by weight, preferably from about 1 to 10 percent, by weight, of the total composition, are effective for treating the fungal infection.

Various antifungal agents suitable for use in this invention are mentioned above. Preferred antifungal agents that can be administered according to this invention include abafungin, albaconazole, amorolfine (dimethylmorpholine), AN2690 (an oxaborate), benzalkonium chloride, bifonazole, butenafine, butoconazole, caspofungin, cetrimide, cetylpyridinium chloride, clioquinol, ciclopirox olamine, clotrimazole, copper sulfate, econazole, fluconazole, gentian violet, haloprogin, hypochlorous acid/bleach, IDP-108, itraconazole, ketoconazole, luliconazole, LY-303366 (echinocandins), miconazole, naftifine, nitric oxide, oxiconazole, oxychlorosene sodium, pramiconazole, posaconazole, povidone-iodine, ravuconazole, sertaconazole, sulconazole, terbinafine, terconazole, tioconazole, tolnaftate, undecylenic acid, and voriconazole, and compatible combinations thereof.

The present composition and method can also use a keratolytic agent to facilitate diffusion or migration of the medication through the subungal debris, caused during the above-described onycholysis. Suitable keratolytic agents include urea (5-40%), salicylic acid (5-40%), DMSO, sulfur, and other known compounds. Acid and/or enzymatic keratolytics can be used. The acids include the alpha-hydroxy acids (such as lactic acid), beta-hydroxy acids (such as salicylic acid), and their derivatives, such as keto-hydroxy acids, including the root moieties glycolic, lactic, pyruvic, and citric. In addition, such derivatives can include salts, such as ammonium lactate (commercially available as LacHydrin™). Examples of enzymatic exfoliants useful in the compositions and methods of the invention include, but are not limited to, papain, from papaya, and bromalein, from pineapple. Examples of acidic exfoliants include, but are not limited to a mono- or poly-hydroxy acid, tannic acid, or a mixture thereof, or a pharmaceutically acceptable salt or ester thereof. One of ordinary skill in the art will be readily able to select and prepare suitable mono- or poly-hydroxy acids for use in the composition of the invention, for example, alkyl hydroxycarboxylic acids, aralkyl and aryl hydroxycarboxylic acids, polyhydroxy-carboxylic acids, and hydroxy-polycarboxylic acids. One of ordinary skill in the art would typically select one or more of the following mono- or poly-hydroxy acids: 2-hydroxyacetic acid (glycolic acid); 2-hydroxypropanoic acid (lactic acid); 2-methyl 2-hydroxypropanoic acid; 2-hydroxybutanoic acid; phenyl 2-hydroxyacetic acid; phenyl 2-methyl 2-hydroxyacetic acid; 3-phenyl 2-hydroxyacetic acid; 2,3-dihydroxypropanoic acid; 2,3,4-trihydroxybutanoic acid; 2,3,4,5,6-pentahydroxyhexanoic acid; 2-hydroxydodecanoic acid; 2,3,4,5-tetrahydroxypentanoic acid; 2,3,4,5,6,7-hexahydroxyheptanoic acid; diphenyl 2-hydroxyacetic acid; 4-hydroxymandelic acid; 4-chloromandelic acid; 3-hydroxybutanoic acid; 4-hydroxybutanoic acid; 2-hydroxyhexanoic acid; 5-hydroxydodecanoic acid; 12-hydroxydodecanoic acid; 10-hydroxydecanoic acid; 16-hydroxyhexadecanoic acid; 2-hydroxy-3-methylbutanoic acid; 2-hydroxy-4-methylpentanoic acid; 3-hydroxy-4-methoxyrnandelic acid; 4-hydroxy-3-methoxymandelic acid; 2-hydroxy-2-methylbutanoic acid; 3-(2-hydroxyphenyl) lactic acid; 3-(4-hydroxyphenyl) lactic acid; hexahydromandelic acid; 3-hydroxy-3-methylpentanoic acid; 4-hydroxydecanoic acid; 5-hydroxydecanoic acid; aleuritic acid; 2-hydroxypropanedioic acid; 2-hydroxybutanedioic acid; erythraric acid; threaric acid; arabiraric acid; ribaric acid; xylaric acid; lyxaric acid; glucaric acid; galactaric acid; mannaric acid; gularic acid; allaric acid; altraric acid; idaric acid; talaric acid; 2-hydroxy-2-methylbutaned-ioic acid; citric acid, isocitric acid, agaricic acid, quinic acid, glucoronic acid, glucoronolactone, galactoronic acid, galactoronolactone, uronic acids, uronolactones, ascorbic acid, dihydroascorbic acid, dihydroxytartaric acid, tropic acid, ribonolactone, gluconolactone, galactonolactone, gulonolactone, mannonolactone, citramalic acid; pyruvic acid, hydroxypyruvic acid, hydroxypyruvic acid phosphate and esters thereof; methyl pyruvate, ethyl pyruvate, propyl pyruvate, isopropyl pyruvate; phenyl pyruvic acid and esters thereof; methyl phenyl pyruvate, ethyl phenyl pyruvate, propyl phenyl pyruvate; formyl formic acid and esters thereof; methyl formyl formate, ethyl formyl formate, propyl formyl formate; benzoyl formic acid and esters thereof; methyl benzoyl formate, ethyl benzoyl formate and propyl benzoyl formate; 4-hydroxybenzoyl formic acid and esters thereof; 4-hydroxyphenyl pyruvic acid and esters thereof, and 2-hydroxyphenyl pyruvic acid and esters thereof.

As mentioned above, acceptable salts of the foregoing acids can be used as keratolytic agents. Examples of suitable inorganic metallic bases for salts formation with the acid compounds of the invention include, but are not limited to, ammonium, aluminum, calcium, lithium, magnesium, potassium, sodium, and zinc. Appropriate organic bases may be selected, for example, from N,N-dibenzylethylenediamine, chloroprocaine, choline, diethanolamine, ethylenediamine, meglumaine (N-methylglucamine), and procaine. It should be understood that one or more derivatives of the above acidic component, such as esters or lactones thereof, are also suitably used. One of ordinary skill in the art will also understand that various hydroxy acids described in U.S. Pat. Nos. 5,547,988 and 5,422,370, are also suitable for use in the compositions and methods of the invention. The acidic component is present in the composition and methods in an amount sufficient to exfoliate, i.e., remove dead or dying cells, from at least a portion of the nail bed. The acidic component is typically present in an amount from about 0.1 to 12 weight percent, preferably about 1 to 11 weight percent, more preferably from about 4 to 10 weight percent of the composition. For example, the acidic component may be present from about 0.1 to 3 weight percent citric acid in combination with up to about 2 weight percent salicylic acid.

The instant composition is preferably applied between twice daily and once weekly, more preferably between once daily and once every three days. It is also preferred that the doses be self-administered.

Depending on the individual patient's or practitioner's preference, the subunguicide can be administered in the various forms mentioned above. The subunguicide can be administered in a low viscosity flowable form, in which case the device for administering will include a small cannula having sufficient rigidity to be introduced proximal to the hyponychium for delivery of the drug to the nail bed. Such a device can be a hypodermic needle 201 (essentially a cannula having an integral trocar attached to a piston-pressurized or bulb-pressurized reservoir) as shown in FIG. 2A. Also depicted is the effect of onycholysis, the separation of the nail plate from the nail plate starting at the distal end and resulting in a gap 209 between the nail plate and the nail bed that, in a healthy nail, would be sealed by the hyponychium. The relatively low viscosity of such a flowable form is generally less than about 1000 P (100,000 centipoise), and preferably is not dilatant in order to allow use with a piston and hypodermic needle. The administered formulation is shown as 99, and can be colored to provide, even through the nail plate, a visual indication of coverage of the nail bed after administration and preferably after migration. FIG. 2B depicts another embodiment of a device for delivering a low or medium viscosity subunquicide. A single-use packet 211 has a relatively rigid backing 213 upon which is formed (such as in the manufacture of blister packs) an overlying flexible wall 215 to provide a reservoir (i.e., a bulb-pressurized reservoir). Alternatively, two flexible walls can be fused or molded together that meet at a seam. Formed integrally is cannula 217 for administration of a subunguicide liquid or paste in the reservoir. The end of the cannula is preferably molded to be closed, whereby the user need only cut off the end to use the device. As shown in FIG. 2A, the cannula is introduced between the hyponychium and the nail plate.

FIG. 2C depicts the subunguicide in the form of a paste 221 forced between the hyponychium and the nail plate with a spatula 223. A paste is used herein to mean a high viscosity fluid, having a viscosity greater than about 1000 P (from the viscosity approximate that of tomato paste or peanut buffer up to that of putty). Beyond that and also suitable for use in this invention are semisolids having effective viscosities over 10,000 P, where the viscosity is typically measured using a penetration test (for example, U.S. Pat. Pub. 20060112503, for a stick deodorant, appears to use an ASTM test for the viscosity of bituminous materials like asphalt). Administration of a subunguicide in the form of a semisolid (like a deodorant stick) and solids softer than a human nail (like a bar of soap) is shown in FIG. 2D, wherein the patient scratches the surface of the solid or semisolid 231 with sufficient force to propel shavings past the hyponychium and to rest in contact with the nail bed. A solid or semisolid formulation self-administered by scratching has a Mohs hardness less than 2.5 and is sufficiently cohesive that the shavings will be forced past the hyponychium to reside on the nail bed. While this mode of administration may be not advisable if the severity of the onycholysis makes loss of the nail plate possible due to the force required, the softness (viscosity) of the subunguicide in this form can be varied as desired.

Figure 3A:
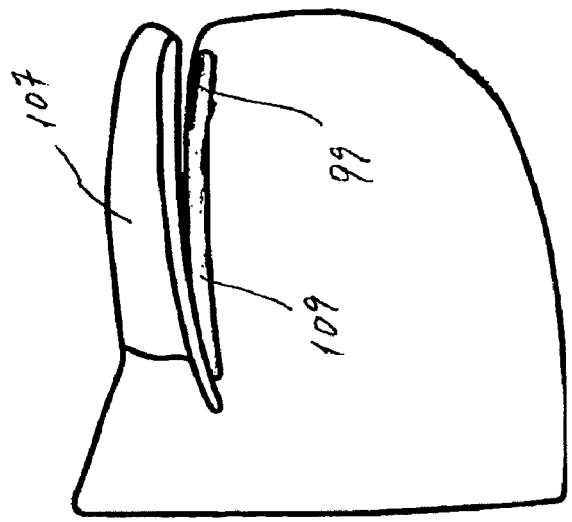
FIGS. 3A through 3C are depictions over time, and with repeated administration, of the migration of the administered subunguicide along the nail bed.
Figure 3B:
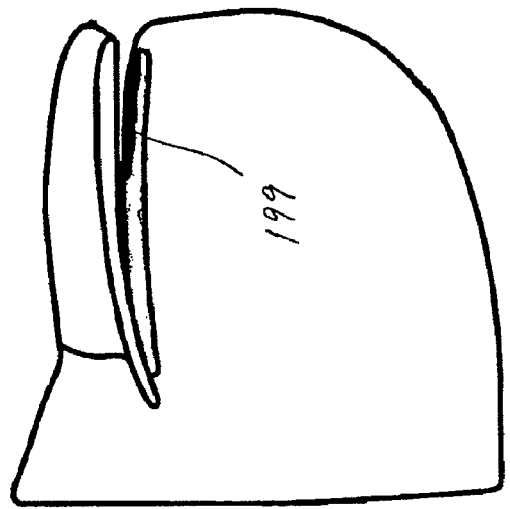
Figure 3C:
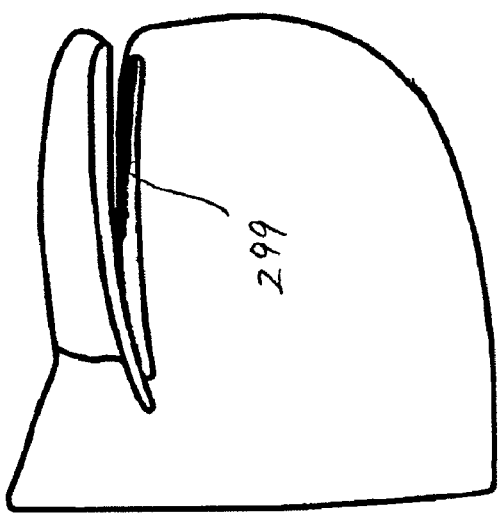

The carrier base used to formulate the subunguicide can be chosen to soften or more preferably liquefy at body temperature (such as a petrolatum) so that the material tends to flow over the nail bed after administration. The chronology shown in FIGS. 3A through 3C depicts migration of the initially applied subunguicide 99 spreading over the nail bed to cover more proximal portions 199 and continuing to cover more proximal and lateral portions 299 of the nail bed. The existence of onycholysis facilitates the migration of the subunguicide proximally.

In yet another embodiment, the subunguicide can be produced in the form of a semisolid or solid disposed in the orifice of a cannula (e.g., a hypodermic needle) and after introduction of the cannula adjacent the nail bed, and inserted as the cannula is retracted to leave behind a dose of the subunguicide.

Preferred semisolid or solid matrices are based on a high molecular weight hydrocarbon, such as a wax, preferably a microcrystalline wax. Ingredients, including the active ingredient and non-active ingredients, preferably are added to the wax while the wax is in a molten state. Compositions that are liquid at room temperature, such as oils, can be added to soften the solidified wax. By solid and semisolid are meant a composition that, as provided in use, has a three dimensional geometry such that a patient's nails can be dug in to the bulk matrix, and which may include an ingredient that, if dissolved and present in a liquid form would form a film, yet in the present invention is provided dispersed in a bulk solid or semisolid matrix. The solid or semisolid matrix preferably comprises at least 40% w/w, more preferably at least 60% w/w, of the total composition.

In contrast, liquid formulations useful in the present invention are intended to exclude any significant amount of a film-forming agent (e.g., a dissolved polymer conventionally used as a film former). As noted in the Background, prior art formulations are often applied as a lacquer or coating to the exterior surface of the nail plate. Liquid vehicles preferably include short chain alcohols (such as ethanol or isopropanol) and liquid short chain diesters (such as diisopropyl adipate and diethylhexyl (or dioctyl) adipate).

A liquid, solid, or semi-solid formulation may also include a non-volatile polar solvent, such as propylene glycol, hexylene glycol, benzyl alcohol, PEG 300, or diethylene glycol monoethyl ether, and compatible mixtures thereof. The non-volatile solvent, if present, is generally present in an amount of 0.5-25 wt %, and more preferably at 1.0-15 wt %.

As shown below, a liquid formulation having the active ingredient can be admixed into a solid or semisolid ultimate formulation, the solid or semisolid matrix optionally having the same or a different active ingredient (and/or inactive ingredient).

A formulation that is solid or semisolid at room temperature (e.g., 25° C.) that is liquid or significantly more flowable at body temperature (~37° C.) can be administered as a heated, liquid form, preferably at a temperature close to body temperature.

EXAMPLE 1

Terbinafine Free Base Preparation

Terbinafine free base was prepared by adding 2.0 g of terbinafine HCl to 8.0 g of isopropyl alcohol (IPA) and 4.0 g Dowex Marathon A OH ion exchange resin. This resin exchanges OH$^-$ for Cl$^-$ and was washed with IPA prior to use. With the Cl$^-$ removed from solution, the free base formed and the terbinafine went into solution within 5-10 minutes. (Terbinafine HCl is soluble in IPA up to 3.7%.) The reaction with the resin was run for 4 hours. Presence of the free base was confirmed by adding a drop of this IPA solution into water and measuring pH with a color strip. Adding the IPA solution caused the water pH to increase approximately one unit. The resin added OH$^-$ to the solution, which reacted with H$^+$ and increased the water content. Excess water was removed by storing the terbinafine free base solution over molecular sieves for one week.

EXAMPLE 2

Solid Carrier Consistency

Using microcrystalline wax, NF (193/198 from Koster Keunen Inc., Watertown, Conn.) and hydrogenated vegetable oil, NF (Weccobe S from Stepan Chemical, Northfield, Ill.), three formulations were made and tested for hardness (durometer readings using instruments from Rex Gauge Company, Inc., Buffalo Grove, Ill.) and for their ability to be scratched with forcing of the carrier past the hyponychium.

| Composition | Evaluation | Durometer Scale | Durometer Reading |
|---|---|---|---|
| 100 wt % wax | too firm | DO | 80 |
| 50:50 wax:oil | needs to be firmer | O | 60 |
| 75:25 wax:oil | good consistency | O | 85 |

EXAMPLE 3

Solid Terbinafine Composition

A terbinafine HCl solid formulation was prepared using:
10.0% terbinafine HCl
67.5% microcrystalline wax
22.5% hydrogenated vegetable oil
0.1% Sorbitan sesquioleate
(Microcrystalline wax was 193/198 from Koster Keunen Inc., Watertown, Conn. Hydrogenated vegetable oil was Weccobe S from Stepan Chemical, Northfield, Ill.)

The excipients were added to a Pyrex beaker, heated to ~60-70° C., and mixed until a homogeneous solution formed. A thin layer of this hot solution was poured into a square plastic mold and cooled to room temperature. The solid/semisolid matrix was carefully removed from the mold after 1-2 hours at room temperature. The terbinafine HCl was part of the matrix and was added to the melt along with a surfactant prior to pouring into the mold. Because terbinafine HCl was not soluble in the melt, it was gently ground in a mortar and pestle before addition to the melt.

The resin added OH$^-$ to the solution which reacted with H$^+$ from the terbinafine HCl to increase the water content. Excess water was removed by storing the terbinafine free base solution over molecular sieves for one week. A sample of the solution was assayed by HPLC to determine the terbinafine content.

EXAMPLE 4

Release Properties of Solid Formulation

Samples of the solid prepared in Example 2 were divided into the small cubes ~1-2 mm per side that weighed ~200 mg each (~20 mg of terbinafine HCl/cube). Each cube was added to a separate container with 20 mL of distilled water and closed. Three samples (cubes) from the batch were tested. The cubes floated on the water and it appeared that >80-90% of the surface was in contact with the water. The containers were held at 37° C. without any stirring. After 24 and 48 hours, the containers were gently swirled to make sure the solution was homogeneous, and a sample was removed and assayed for terbinafine HCl and the % released calculated. After 24 hours, approximately 15% (±5%) of the terbinafine HCl had leached from the cube, and after 48 hours, approximately 28% (±5%) had leached.

This example establishes proof of principle. In the actual treatment, the solid formulation will have a geometry more sheet-like, with a higher surface area, and so the leach rate would be expected to be greater than in this example.

EXAMPLE 5

Liquid Terbinafine HCL Formulations

TABLE 1

| | all values % w/w | | | | |
|---|---|---|---|---|---|
| Ingredient | Ex. 5A | Ex. 5B | Ex. 5C | Ex. 5D | Ex. 5E |
| Terbinafine HCl | 1.0 | 10.0 | 5.0 | 2.5 | 5.0 |
| Isopropanol | 81.0 | — | 42.5 | 79.5 | 52.0 |
| Ethanol | — | 80.0 | 42.5 | — | 25.0 |
| Dimethicone | 5.0 | — | — | 5.0 | 5.0 |
| Cyclomethicone | 13.0 | — | 10.0 | 13.0 | 13.0 |
| Diisopropyl adipate | — | 10.0 | — | — | — |

A slight phase separate for Ex. 5E was observed after 10 days storage at room temperature.

EXAMPLE 6

Terbinafine Liquid Formulation

Terbinafine HCl salt was dissolved in water (~1 mg/mL) and neutralized with 1.0M NaOH. A precipitate rapidly formed, but it was fine colloidal "oil" droplets rather than a coarse solid. Extraction with diethyl ether and evaporation yielded only minute quantities of free base. The ion exchange process described above (Ex. 1) was successfully used to make solutions of terbinafine free base in isopropanol. After assay, an appropriate amount of the free base concentrate was added to the remaining excipients to prepare a solution equivalent to 10% terbinafine HCl:

8.85% terbinafine free base (equivalent to 10% terbinafine HCl)
  5.0% dimethicone
  13.0% cyclomethicone
  73.15% isopropyl alcohol This solution had a high level of terbinafine with the good spreading properties of a isopropanol/silicone oil formulation.

EXAMPLES 7a, 7b, 7c, and 7c

Effective Antifungal Activity

An inoculum size of 3×10$^6$ colony forming units/ml of a terbinafine-susceptible *T. rubrum* was prepared in 0.85% sterile saline, and then used to inoculate potato dextrose agar plates.

Ex. 7a: A wax-based formulation was prepared having 2.5% terbinafine using the procedure described in Ex. 3, and a shaving from this formulation was placed on an inoculated plate. After incubating for 96 hours at 30° C., a zone of inhibition of ~30 mm was seen.

Ex. 7b: Ex. 7a was repeated with incubation at 37° C. After 96 hours, complete inhibition of growth (zone of inhibition greater than 89 mm) was observed.

Ex. 7c: An 8 mm punch biopsy was removed from the approximate center of an inoculated plate to form a well, and 200 µl of a liquid formulation of 2.5% terbinafine HCl (from Ex. 5D) was added to the well. Complete inhibition of growth (inhibition zone greater than 89 mm) was seen after incubation for 96 hrs. at 30° C.

Ex. 7d: An 8 mm punch biopsy was removed from the approximate center of an inoculated plate to form a well, and 200 µl of a liquid formulation of 8.85% terbinafine (Ex. 6) from was added to the well. Complete inhibition of growth (inhibition zone greater than 89 mm) was seen after incubation for 96 hrs. at 30° C.

The normal body temperature under the nail plate is usually at least 32° C., up to about 37° C. Accordingly, in vivo inhibition of the infective fungus using the present invention is expected to be better than seen in Ex. 7a. Existence of poor circulation or the situation of prolonged exposure to cold (such as in snow or cold water) may reduce the temperature under the nail plate to less than about 30° C. In such cases, this invention provides a method for treating onychomycosis in an affected digit, comprising providing a subunguicide including an antifungal agent in a suitable solid or semi-solid carrier, and administering the same subungually by forcing the subunguicide between the hyponychium and the nail plate and past the hyponychium to be in contact with the nail bed, and heating or warming the distal region of the digit containing the applied subunguicide to between about 32° C. and about 37° C. Heating or warming can be accomplished by bandaging and wrapping with a wet heated cloth, providing a finger cot formed in a pouch having a heatable gel (such as cosmetics masks that can be heated in a microwave oven or chilled in a refrigerator), or wearing multiple layers and wool (or other good insulating) socks. While it may be impractical to maintain heating or warming continuously for 96 hours, heating or warming only during sleeping or sedentary times (as examples) will aid in resolving the infection, and so the heating or warming need not be continuously maintained to improve the antifungal effect when using a solid or semi-solid carrier.

The foregoing examples are intended to be illustrative and not limiting. The preferred vehicle for a non-liquid (semi-solid or solid) formation is a combination microcrystalline wax ("MCW") and hydrogenated vegetable oil ("HVO"), most preferably at a ratio of about 3:1 (w/w), preferably between 4:1 and 2:1. For liquid formulations, ethanol is most preferred for terbinafine HCl and other acid salts and free acids of antifungal agents, and isopropanol is most preferred for terbinafine free base and other free base or basic salts of antifungal agents. Silicone oils (e.g., dimethicone) can be added to provide desired spreading properties. Surfactants can be added as emulsifying agents for liquid or non-liquid formulations. Various changes, modifications, and additions may become apparent to the skilled artisan upon a perusal of this specification, and such are meant to be within the scope and spirit of the invention as defined by the claims.

What is claimed is:

1. A non-liquid subunguicide comprising an antifungal agent terbinafine hydrochloride salt and a non-soap semisolid carrier comprising at least 60% by weight of a microcrystalline wax and also comprising a hydrogenated vegetable oil, where the w/w ratio of the wax and the oil is between 2:1 and 4:1, wherein the composition has a Mohs hardness of less than 2.5 and is sufficiently cohesive that the shavings will be forced past the hyponychium to reside on the nail bed.

2. The subunguicide of claim 1, further comprising a surfactant for emulsifying the antifungal agent.

3. The subunguicide of claim 1, further comprising a non-volatile polar solvent in an amount of between about 0.5% and 15% by weight.

* * * * *